United States Patent [19]
Phillips et al.

[11] Patent Number: 4,642,099
[45] Date of Patent: Feb. 10, 1987

[54] INJECTOR

[75] Inventors: Ian R. Phillips, Killara; Robert H. Lodge; Glen W. Bunyan, both of Dee Why, all of Australia

[73] Assignee: N.J. Phillips Pty. Limited, New South Wales, Australia

[21] Appl. No.: 760,394

[22] Filed: Jul. 30, 1985

[30] Foreign Application Priority Data

Jul. 31, 1984 [AU] Australia .............................. PG6304

[51] Int. Cl.⁴ .............................................. A61M 5/20
[52] U.S. Cl. ..................................... 604/136; 604/198
[58] Field of Search ............... 604/134, 135, 136, 137, 604/192, 198, 133

[56] References Cited

U.S. PATENT DOCUMENTS 3,797,489  3/1974  Sarnoff ................................. 604/136
4,403,989  9/1983  Christensen et al. ................. 604/137

FOREIGN PATENT DOCUMENTS

A10074836  3/1983  European Pat. Off. .
EP074836   3/1983  European Pat. Off. .
  805184  12/1958  United Kingdom .
  969781   9/1964  United Kingdom .
  979124   1/1965  United Kingdom .
 1263355   2/1972  United Kingdom .
 2132488   7/1984  United Kingdom .

Primary Examiner—John D. Yasko
Attorney, Agent, or Firm—Ladas & Parry

[57] ABSTRACT

A rumen injector having a body, an interacting piston and cylinder mounted within the body, a needle fixed to the cylinder, and wherein the cylinder is movable from a rest position to a cocked position and said piston is movable within said cylinder from a rest position to a cocked position so that in use of the injector said cylinder is first released to cause insertion of the needle and then said piston is released to cause injection of a dose into the rumen of the animal.

9 Claims, 3 Drawing Figures

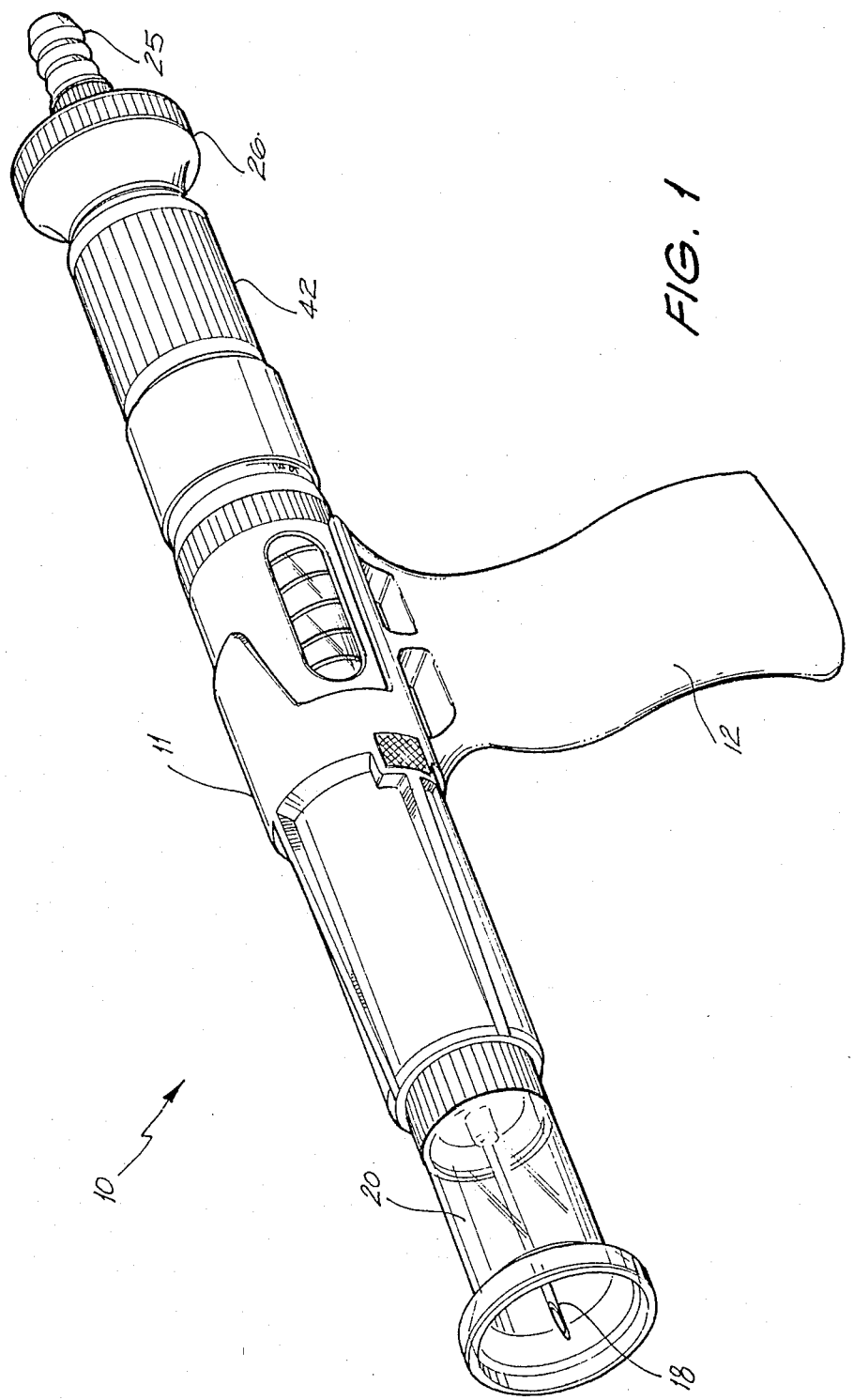

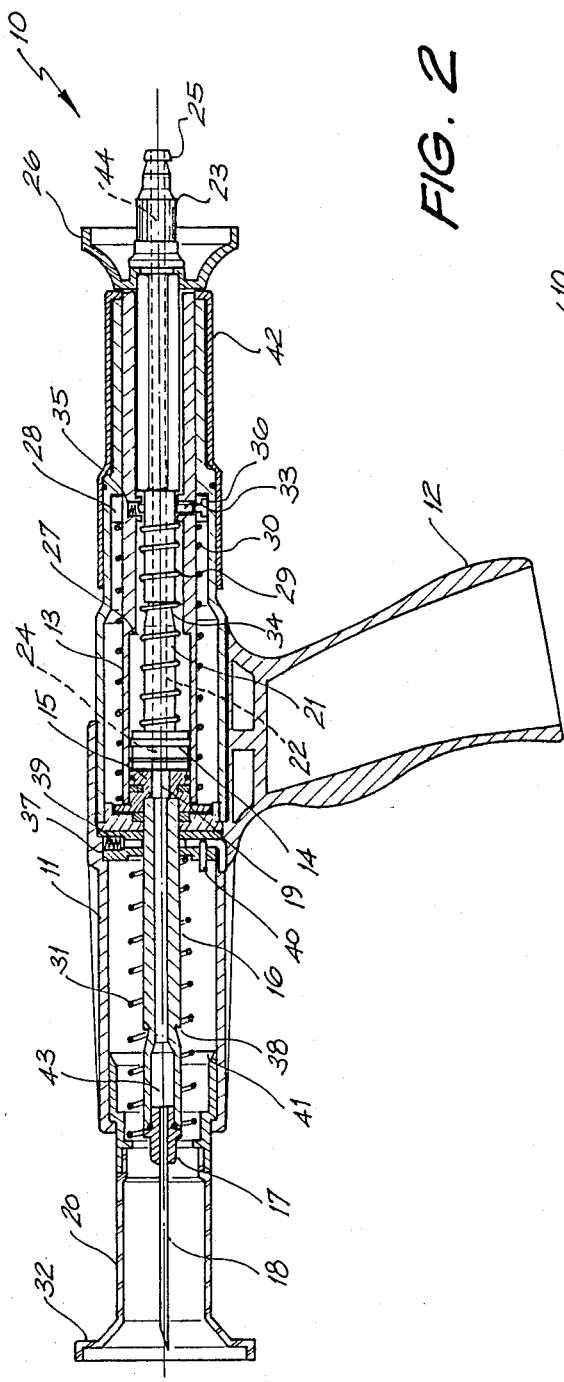
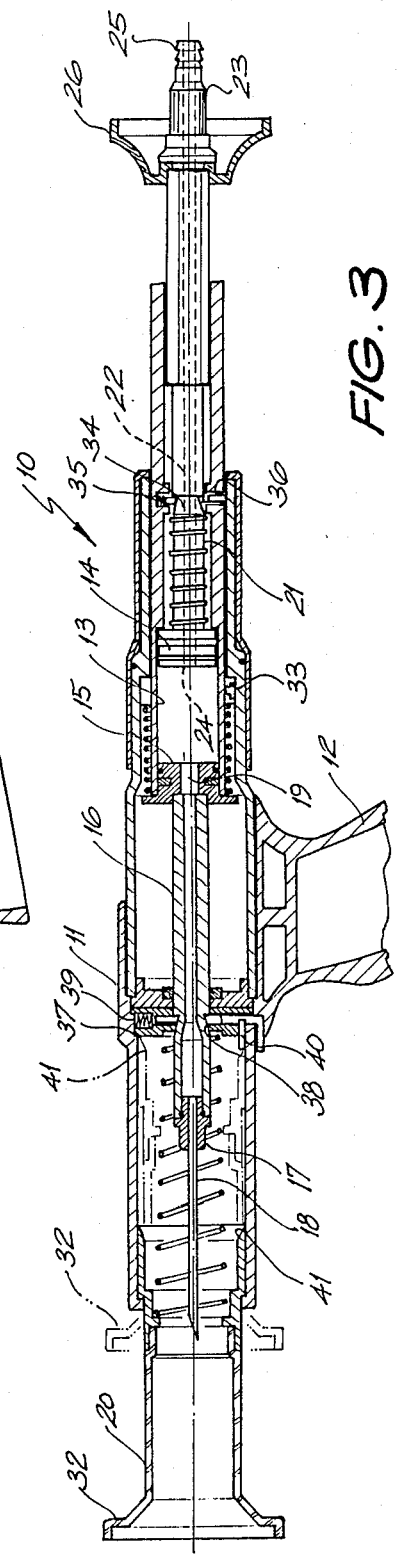

INJECTOR

The present invention relates to injecting or drenching apparatus used to dispense a required dose to an animal. More particularly, but not exclusively, the present invention relates to rumen injectors.

Known injecting apparatus require the use of a trigger or similar arrangement to which the user must apply a force to operate the device in order to deliver a desired dose unit to an animal. Alternatively, a needle is inserted and a cocking mechanism released so that a dose is delivered. The first of these known devices requires two actions, firstly the apparatus must be maintained at a desired location relative to the animal, and secondly the user must operate the device in order to deliver the dose to the animal. The second type of known apparatus requires the user to apply sufficient force to the apparatus to insert the needle. Accordingly, these known apparatus have the disadvantage of requiring considerable coordination or effort to insert the needle.

It is the object of the present invention to overcome or substantially ameliorate the above disadvantages.

There is disclosed herein An injector to deliver a required dose into an animal, said injector comprising a hollow body, an interacting piston and cylinder cooperating to define a variable volume working space, said cylinder being longitudinally movable of said body between a cocked position and a rest position, said piston being movable within said cylinder between a cocked position defining a maximum volume for said space and a rest position defining a minimum volume for said space, a dose delivery means including a needle fixed to the said cylinder or piston and communicating with said space so that upon a reduction in volume thereof a dose is delivered through said delivery means, first spring means biasing said cylinder to its rest position, second spring means biasing said piston to its rest position, first retaining means to selectively retain said cylinder in its cocked position and operable to release said cylinder, second retaining means to selectively retain said piston in its cocked position and operable to release said piston, and release means actuable to operate said first retaining means to release said cylinder and operate said second retaining means to release said piston such that said space is only reduced in volume after said needle has been injected into said animal a predetermined distance.

A preferred form of the present invention will now be described by way of example with reference to the accompanying drawings wherein:

FIG. 1 is a schematic perspective view of a rumen injector;

FIG. 2 is a schematic part sectioned side elevation of the injector of FIG. 1; and FIG. 3 is a schematic sectioned side elevation of the injector of FIG. 1 in a cocked position.

In FIGS. 1 to 3 there is schematically depicted a rumen injector 10. The injector 10 has a hollow body 11 providing a handle 12 to be gripped by a user when delivering a dose to an animal. Mounted within the body 11 is a cylinder 13 within which there is slidably mounted a piston 14. The cylinder 13 is closed at one end by a plug 15. The cylinder 13, piston 14 and plug 15 cooperate to provide a variable volume working space with the volume thereof being determined by the position of the piston 14 longitudinally of the cylinder 13.

The cylinder 13 is also movably mounted within the body 13 so as to be movable from a rest position, as depicted in FIG. 2, to a cocked position, as depicted in FIG. 3, spaced towards the rear of the gun from the rest position. Fixed to the plug 15 so as to extend forwardly therefrom is a tube 16 provided at its free end with a needle mounting member 17. Fixed to the member 17 is an injector needle 18. Extending through the plug 15 is a passage 19 so as to provide communication between the abovementioned variable volume space and the needle 18 so that upon reduction of the variable volume space a dose is delivered through the needle 18 into the animal. Mounted on the forward end of the body 11 is a retractable shroud 20 which is movable from the position depicted in FIG. 2 to retracted position exposing the needle 18.

Extending from the piston 14 is a piston rod 21 providing a passage 22 communicating with an inlet adaptor 23. The piston 14 is provided with a passage 24 so that the passage 22 can deliver a liquid to be injected to the variable volume space mentioned above. The adaptor 23 is provided with a spigot 25 to which a flexible tube may be connected so that the injector 10 may be connected to a supply of liquid. There will also be provided a one way valve either in the container providing the bulk supply of liquid, the tube connected to the spigot 25, or within the piston rod 21, which would determine the direction of movement of the liquid being delivered by the injector 10, that is to move from the spigot 25 to the needle 18. Preferably one way valve assemblies would be located in the cavities 43 and 44. The valve in the cavity 43 being provided to enable refilling. The adaptor 23 is provided with a shield 26 enabling a user of the injector 10 to grip the shield 26 so as to move the piston rod 21 from the position depicted in FIG. 2 to the cocked position spaced towards the rear of the body 11. The cocked position of the piston 14 is defined by a lip 27 formed on the internal peripheral surface of the cylinder 13. Upon the piston 14 engaging the lip 27, and upon the operator continuing movement of the shield 26, the cylinder 13 is also moved to a cocked position defined by the sleeve 28. Biasing the piston 14 to the rest positibn depicted in FIG. 2 is a spring 29 while biasing the cylinder 13 to the rest position depicted in FIG. 2 is a spring 30. A further spring 31 is provided to bias the shield 20 to a position covering the needle 18 as depicted in FIG. 2. However, it should be appreciated that the shield 20 is retractable to a position substantially telescopically located within the body 11 apart from the flaired end 32 of the shield 20.

To selectively retain the piston 14 in the cocked position, there is provided a retaining member 33 which cooperates with an abutment in the form of a lip 34 formed on the piston rod 21. The member 33 is biased by a spring 35 to a position of engagement with the lip 34 but is movable against the spring 35 so as to release the piston rod 21. To move the retaining member 33 to a release position, there is provided a cam in the form of a release member 36 mounted in the sleeve 28. The release member 36 engages the retaining member 33 so as to move it against the spring 35 so that the lip 34 is released.

To retain the cylinder 13 in the cocked position there is provided a retaining member 37 which cooperates with an abutment in the form of a lip 38 formed on the tube 16. The release member 37 is biased into engagement with the lip 38 by means of a spring 39. However, it should be appreciated that the retaining member 37 is movable against the spring 39 so as to release the lip 38. Fixed to the retaining member 37 is a projection 40 which is engaged by a ramp surface 41 formed on the internal edge of the shield 20. The ramp surface 41 engages the projection 40 so as to cause movement of the retaining member 37 against the spring 39.

Rotatably mounted on an external surface of the body 11 is an adjustment sleeve 42 which threadably engages the body 11 so as to be movable longitudinally thereof in an adjustment manner so as to abut the shield 26. By longitudinally moving the sleeve 42, by rotation about the longitudinal axis of the body 11, the amount of movement of the piston towards the rest position depicted in FIG. 2, may be adjusted to adjust the volume of the liquid delivered by the injector 10.

In operation of the abovedescribed injector 10, the dose size is selected by rotation of the sleeve 42. Thereafter, the operator grips the shield 26 and pulls on the shield 26 so as to cause cocking of the piston 14 and then cocking of the cylinder 13. The piston 14 and cylinder 13 are then retained in the cocked position by the retaining members 33 and 37. When an animal is to be injected, the operator grips the handle 12 and places the end 32 of the shield 20 against the animal's skin. Upon an application of a force to the handle 12, the shield 20 is telescopically moved, as shown in ghost lines in FIG. 3, back into the body 11 causing compression of the spring 31. Upon the shield 20 reaching a predetermined position within the body 11, and the surface 41 engaging the projection 40, the cylinder 13 is released and the needle caused to penetrate the animal. Upon the cylinder 13 moving a predetermined distance along its longitudinal axis, the retaining member 33 mounted in the cylinder 13, engages the release member 36 so as to release the piston 14. Upon the piston 14 being released, the working space defined within the cylinder 13 is reduced in volume thereby forcing liquid out through the needle 18 thereby delivering the dose to the animal.

It should be appreciated that in the above preferred embodiment the piston 14 is fixed to the piston rod 21. however the positions of the cylinder 13 and piston 14 could be reversed, that is the cylinder fixed to the piston rod 2. In this modified configuration the needle 18 would be fixed to the piston 1.

What we claim is:

1. An injector to deliver a required dose into an animal, said injector comprising a hollow body, a movable assembly including an interacting piston and cylinder cooperating to define a variable volume working space, said assembly being longitudinally movable of said body between a cocked postion and a rest position, said piston and said cylinder being movable relative to each other between a cocked position defining a maximum volume for said space and a rest position defining a minimum volume for said space, a dose delivery means including a needle fixed to the said assembly and communicating with said space so that upon a reduction in volume thereof a dose is delivered through said delivery means, first spring means biasing said assembly to its rest position, second spring means to cause relative movement between said piston and cylinder to the rest position thereof, first retaining means to selectively retain said assembly in its cocked position and operable to release said assembly to cause insertion of said needle, second retaining means mounted on said assembly to selective retain said piston and cylinder, in the cocked position thereof and operable to release said piston and cylinder, first release means actuable to operate said first retaining means to release said assembly, second release means mounted on and fixed to said body to operate said second retaining means to release said piston and cylinder, and wherein said second release means is positioned to engage said second retaining means only after said needle has been injected into said animal at a predetermined distance.

2. The injector of claim 1 wherein said needle is fixed to said cylinder, a piston rod extends from said piston, said second spring means biases said piston to move relative to said cylinder and said second retaining means retains said piston stationary with respect to said cylinder until said piston is released upon operation of said second retaining means by said second release means.

3. The injector of claim 2 wherein said first release means includes a shroud movably mounted on said body and generally surrounding said needle, said shroud is movable from an extended position to a retracted position telescopically located within said body.

4. The injector of claim 3 wherein said first retaining means includes a first abutment fixed to said cylinder and a first retaining member movably mounted in said body and operably associated with said first abutment to selectively retain said assembly in the cocked position thereof, said second retaining means includes a second abutment formed in said piston rod and a second retaining member movably mounted on said cylinder and operably associated with said second abutment to retain said piston in the cocked position thereof relative to said cylinder, with said second release member being positioned to selectively engage said second retaining member to cause movement thereof.

5. The injector of claim 4 wherein said shroud causes operation of said first retaining member upon reaching a predetermined position telescopically located within said body.

6. The injector of claim 5 wherein said second release means includes cam means mounted on said body to cause movement of said second retaining member when said assembly reaches the rest position thereof.

7. The injector of claim 6 further including adjustment means to limit the travel of said piston within said cylinder to thereby adjust the volume of the dose delivered by the injector.

8. The injector of claim 7 further including a wall closing one end of said cylinder, a tube extending from said wall and upon which said needle is mounted, and said delivery means includes a passage extending through said wall and said tube.

9. The injector of claim 8 wherein said first abutment is formed on said tube.

* * * * *